(12) United States Patent
Veeger et al.

(10) Patent No.: US 6,489,275 B1
(45) Date of Patent: Dec. 3, 2002

(54) SKIN CLEANSING AGENT

(75) Inventors: Marcel Veeger, Goch (DE); Andreas Klotz, Grevenbroich (DE); Bernd Nauels, Kempen (DE)

(73) Assignee: Stockhausen GmbH & Co. KG, Krefeld (DE)

( * ) Notice: Subject to any disclaimer, the term of this patent is extended or adjusted under 35 U.S.C. 154(b) by 0 days.

(21) Appl. No.: 09/665,418

(22) Filed: Sep. 20, 2000

(30) Foreign Application Priority Data

Aug. 18, 2000 (DE) .......................................... 100 40 884

(51) Int. Cl.$^7$ .............................. C11D 1/06; C11D 3/43; C11D 3/20
(52) U.S. Cl. .................. 510/127; 510/119; 510/130; 510/128; 510/137; 510/138; 510/158; 510/159; 510/417; 510/418; 510/505; 510/506
(58) Field of Search ................................ 510/119, 130, 510/137, 138, 158, 159, 417, 418, 505, 506, 127, 128

(56) References Cited

U.S. PATENT DOCUMENTS

| | | | |
|---|---|---|---|
| 5,419,848 A | * | 5/1995 | VanEenam .................. 252/164 |
| 5,538,663 A | | 7/1996 | Kihara et al. |
| 6,075,073 A | | 6/2000 | McGlothlin et al. |
| 6,087,310 A | | 7/2000 | Henkel |

FOREIGN PATENT DOCUMENTS

| | | |
|---|---|---|
| DE | 209 733 | 5/1984 |
| DE | 272 099 | 9/1989 |
| FR | 1 446 790 | 6/1966 |
| WO | WO 00/17300 | 3/2000 |

OTHER PUBLICATIONS

Ullmanns Encyklopaedie der Technischen Chemie, vol. 8, pp. 200, 204, 205 and 207, "Aethylenglykol", (Mar. 1992).

Ullmanns Encyklopaedie der Technischen Chemie, vol. 19, pp. 426 and 428, "Propandiole", (Mar. 1992).

* cited by examiner

Primary Examiner—Gregory Delcotto
(74) Attorney, Agent, or Firm—Oblon, Spivak, McClelland, Maier & Neustadt, P.C.

(57) ABSTRACT

The present invention relates to an agent for cleansing the skin, containing a liquid natural and/or synthetic water-based latex emulsion excluding styrene-butadiene latices, exclusively at least one organic solvent which has a lower volatility than ethanol and a boiling point >78.32° C., and water.

23 Claims, No Drawings

SKIN CLEANSING AGENT

The present invention relates to an agent for cleansing the skin, containing a liquid natural and/or synthetic water-based latex emulsion excluding styrene-butadiene latices, exclusively at least one organic solvent which has a lower volatility than ethanol and a boiling point >78.32° C., and water.

Agents for cleansing the skin, and particularly so-called hand washing pastes with which the dirt is removed without the addition of water, have been familiar for some time. Since with these agents the skin does not have to be rinsed with water after cleansing, there is no need to use a drying cloth.

Well-known from DD 272 099 is a washing paste for the cleansing of oil- and grease-soiled hands which does not require the use of water. The hand washing paste contains 1–3% of an aqueous copolymerizate latex consisting of styrene, 1,3-butadiene, methacrylic acid and a esterification product of the Diels-Alder adducts of maleic acid. WO 00/17300 teaches a skin cleansing agent, which consists of a latex emulsion, an organosilicone compound, emollients, surface-active agents and water. The latex emulsion preferably has a styrene-butadiene copolymer.

The disadvantage of the above-mentioned skin cleansing agents is that they only have limited skin compatibility, are not toxicologically safe and/or pose environmental risks.

The object is therefore to provide a skin cleansing agent which is toxicologically safe, skin-compatible and less harmful to the environment without adversely affecting the cleansing performance.

According to the invention, said object is accomplished by an agent for cleansing the skin which contains a liquid natural and/or synthetic water-based latex emulsion excluding styrene-butadiene latices, exclusively at least one organic solvent which has a lower volatility than ethanol and a boiling point >78.32° C., and water.

According to the invention, the agent for cleansing the skin contains a liquid natural and/or synthetic water-based latex emulsion excluding styrene-butadiene latices. Latex emulsions in the meaning of the invention are dispersions of finely distributed natural and/or synthetic polymers in an essentially aqueous dispersing agent. The polymers comprise natural and synthetic rubber, synthetic resins and/or plastics such as polymerisates, polycondensates and polyaddition compounds. The diameter of the polymer particles preferably is from 0.05 to 5 $\mu$m.

In a preferred embodiment, the agent for cleansing the skin according to the invention contains:
a) 10–80% by weight of a liquid natural and/or synthetic water-based latex emulsion,
b) 1–15% by weight of an organic solvent having a lower volatility than ethanol and a boiling point >78.32° C.,
c) 0–10% by weight of at least one surfactant, preferably at least one fatty alcohol ethoxylate, fatty alcohol ether sulphate, succinate, sarcoside and/or glucoside,
d) 0–10% by weight abrasives, preferably bleached walnut shell meal and/or non-swellable starch,
e) 0–0.1% by weight thickener,
f) optionally, cosmetic adjuvants and additives and/or active ingredients,
g) 10–60% by weight water,
to make a total of 100% by weight.

According to the invention, the agent for cleansing the skin contains an organic solvent with a lower volatility than ethanol and a boiling point >78.32° C., the boiling point being measured at a pressure of 1.013 bar. The solvent is preferably at least one polyhydric alcohol or derivative of a polyhydric alcohol, particularly a polydiol, preferably an alkylene glycol, a polyalkylene glycol, a polydiol derivative, and preferably a polyalkylene glycol ether and/or polyalkylene glycol ester, mono- or polyester of a saturated or unsaturated mono- or polyvalent carboxylic acid with 2 to 30 carbon atoms with n- and isoalkanols with 2 to 10 carbon atoms, preferably a diester of aliphatic and/or aromatic di- and/or tricarboxylic acids, and/or aliphatic hydrocarbon with 12 to 22 carbon atoms, preferably with 16 to 20 carbon atoms and particularly preferably isohexadecane, or a mixture of at least two of the above-mentioned substances.

Preferred polyalkylene glycols or their esters or ethers are listed in the tables from Ullmann, 4th edition, volume 8, pages 200, 204, 205, 207 and volume 19, pages 426 and 428. These tables are hereby incorporated by reference and are thus deemed part of the disclosure.

Dipropylene glycol monomethyl ether is particularly preferred as solvent.

In a preferred embodiment of the present invention, the polymer in the water-based latex emulsion is polyisoprene, which preferably has a cis-1,4 content of at least 90%. The latex emulsion preferably has a solids content of 50 to 80 and especially preferably 60 to 70% by weight. The particle size of the polyisoprene is preferably 1.8 $\mu$m maximum.

The ratio of latex emulsion to solvent is preferably 8:1 to 1:1, and particularly preferably 4:1 to 2:1. These ratios apply extremely preferably if a polyisoprene emulsion is employed as the latex emulsion.

The agent for cleansing the skin can possibly contain a surfactant. This surfactant is preferably a fatty alcohol ethoxylate of general formula: R—O—(CH$_2$—CH$_2$—O)$_n$ with R=C$_{8-18}$ and n=1–8, preferably R=C$_{12-14}$ and n=4–6. The surfactant is also preferably a fatty alcohol ether sulfate of general formula: R—O—(CH$_2$—CH$_2$—O)$_n$SO$_4$X$_2$ with R=C$_{10-16}$ and n=1–4 and X=Na$^+$, K$^+$, ½ Mg$^{2+}$ or NH$_4^+$.

The agent for cleansing the skin preferably contains at least one abrasive. The abrasives can be conventional abrasives or mixtures thereof, and preferably bleached walnut shell meal, non-swellable starch or a mixture thereof.

To modify the consistency of the agent for cleansing the skin according to the invention, the latter can also contain water-swellable polymers as thickeners, where polymers and copolymers obtainable from the polymerization of acrylic acid optionally with other acrylic acid derivatives as comonomers preferably are employed.

The agent for cleansing the skin according to the invention can contain cosmetic adjuvants or additives and/or active ingredients, e.g. care derivatives, emollients, perfume (fragrances), preservatives, etc.

The advantage of the agent for cleansing the skin according to the invention is that it is toxicologically safe and less harmful to the environment. The cleansing performance of the agent for cleansing the skin according to the invention corresponds to those of the prior art. The agent for cleansing the skin according to the invention can be employed in painting installations.

The agent for cleansing the skin according to the invention is particularly suitable as a washing paste. The invention therefore is also directed to the use of the agent for cleansing the skin according to the invention as a washing paste and particularly as a hand washing paste.

The advantage of the use according to the invention is that it is toxicologically safe and less harmful to the environment. The cleansing performance of the agent for cleansing the skin according to the invention corresponds to those of the prior art. The use according to the invention can be beneficially practised in painting installations.

Another object of the present invention is a method for cleansing the skin in which the agent according to the invention is applied to the skin and distributed by rubbing in order to form particles which fall from the hand during further rubbing. The rubbing, for instance when cleansing the hands, takes 10 to 60 seconds and preferably 10 to 30 seconds.

The advantage of the method according to the invention is that it is toxicologically safe and less harmful to the environment. The cleansing performance of the agent for cleansing the skin according to the invention corresponds to those of the prior art. The process according to the invention can be employed in assembly plants, workshops and painting installations, whereby wetting problems on material surfaces are largely avoided.

The invention will be explained below with reference to the Examples. These explanations merely exemplify and do not limit the general idea of the invention.

Test Methods

1. Skin Compatibility Test with the Duhring Chamber Test

This method is an in vivo test model for examining the skin compatibility of various test products in a direct comparison. The products being tested are applied in air-permeable aluminum chambers (18 mm diameter Finn Chambers®) each time to the same test area on the volar side of the lower arms of 20 test subjects on four successive days. The application times are two hours on the first, four hours on the second and six hours on the third and fourth days respectively. The Finn Chambers® are fastened with strips of adhesive plaster. In the event of strong dermal effects, the test is discontinued for each test field before the completion of the overall application time. The skin irritations produced are assessed according to the scale given below and the application times.

R=Reddening (erythema): 0=no erythema, 4=pronounced erythema
P=Peeling: 0=no peeling, 4=pronounced peeling
F=Fissures: 0=no fissures, 4=pronounced fissures The resultant assessment criteria are
a) Irritation as the mean of the sum of irritation values of R, P and F of n test subjects;
b) Application time as the mean of the tolerated application times in hours of n test subjects.

2. Testing Cleansing Performance

Two products are tested in a comparison on at least eight test subjects. Essential for this is that the palms of the hands of all test subjects have a skin structure typically attributable to manual labour. The following test is carried out in the morning and afternoon with one product in each case:

A defined quantity of model dirt (0.2 to 0.5 g) is spread onto the palm and back of the hand and rubbed for 45 s.

It is left to dry for 1½ min.

A defined quantity of the test product (0.3 to 1.8 g) is applied and rubbed in.

Rubbing is continued until the dried product with the collected dirt has been detached from the skin by rubbing and removed.

Visual assessment of the residual soiling (RS) on the back and palm of the hand in accordance with the scale (see below).

0=clean; 5=no cleansing effect (0.5 gradations are possible)

$RS_{palm}$=mean residual soiling of the palm of the hand from n series of measurements (test subjects)

$RS_{back}$=mean residual soiling of the back of the hand from n series of measurements (test subjects)

Composition of a model dirt suitable for the test:

| | |
|---|---|
| Motor oil | 54.15% |
| Vaseline | 18.05% |
| Adeps lanae | 18.05% |
| Graphite | 3.61% |
| Flame soot | 5.42% |
| Iron oxide ($Fe_2O_3$) | 0.72% |

3. Toxicological Test

The toxicological effect of the natural and/or synthetic water-based latex emulsion can be ascertained by determining cytotoxity and by employing the neutral red test.

The test is carried out in accordance with European Standard EN 30 993-5, whereby, with omission of the 72 h incubation period, the test substance is diluted in the cell culture medium and applied to the cells.

The latex emulsion employed was a polyisoprene latex with the designation KRATON® IR-RP 401 from Shell AG.

| Cells | Balb/c 3T3 | Vehicle | DMEM |
|---|---|---|---|
| Dilution | 10% (w/v) | pH | 8.22 |

Neutral Red Uptake

| Concentration (mg/ml) of test substance | 0 | 1 | 2.5 | 5 | 7.5 | 10 | 25 | 50 | 100 |
|---|---|---|---|---|---|---|---|---|---|
| Inhibition (%) of neutral red uptake | | −5.89 | −8.70 | 15.07 | 38.44 | 57.74 | 72.22 | 80.31 | 82.42 |

$NR_{50}$ value:

PT: 7.0 mg/ml (preliminary test)

T: 9.0 mg/ml (test)

Assessment

The tests yield $NR_{50}$ values of 7.0 mg/ml and 9.0 mg/ml respectively. The product can therefore be classified as slightly cytotoxic.

Examples

To test cleansing performance and skin compatibility, 9 hand washing pastes were produced, the compositions of which can be seen in the following Table 1, with the data given in % by weight.

TABLE 1

| Example | 1 | 2 | 3 | 5 | 6 | 7 | 8 | 9 |
|---|---|---|---|---|---|---|---|---|
| Kraton IR 401 latex | 17 | 30 | 50 | 80 | 80 | 30 | 30 | 30 |
| PPG-2 methyl ether | 15 | 10 | 5 | 10 | 5 | | | |
| Di-n-butyl adipate | | | | | | 10 | | |
| PEG 4 | | | | | | | 10 | |
| Hexylene glycol | | | | | | | | 10 |
| Isohexadecane | | | | | | | | |
| Pareth-5 | | 3 | 3 | 3 | | 3 | 3 | 3 |
| Laureth-6 | 1 | | | | 3 | | | |
| Water | 60 | 50 | 35 | 0 | 5 | 50 | 50 | 50 |
| Walnut shell meal | 6 | 6 | 6 | 6 | 6 | 6 | 6 | 6 |
| Thickener | 1 | 1 | 1 | 1 | 1 | 1 | 1 | 1 |
| Total | 100 | 100 | 100 | 100 | 100 | 100 | 100 | 100 |

TABLE 2

| | | | | | | | | |
|---|---|---|---|---|---|---|---|---|
| Skin compatibility | 0 | 0 | + | 0 | + | + | + | + |
| Skin cleansing compared to Castrol Super Clean | + | + | 0 | + | 0 | + | 0 | 0 |

Kraton® IR 401 latex=isoprene latex from Shell Chemicals UT Ltd.
PPG-2 methyl ether=dipropylene glycol monomethyl ether
PEG 4=polyethylene glycol 400 P
Pareth-5=polyethylene glycol ether of a mixture of synthetic $C_9$–$C_{11}$ fatty alcohol (n=5)
Laureth-6=lauryl alcohol polyethylene glycol ether (n=6)
Thickener=Carbopol ETD 2020: acrylic acid copolymer (98–100%)

All the substances given in Table 1 were toxicologically assessed and classified as unproblematical. All the washing pastes given as examples can be employed in painting installations.

The hand washing pastes according to Examples 1–9 were compared to Castrol Super Clean, a Castrol Ltd. product. The results of the comparison are summarized in Table 2, whereby 0 indicates "comparable" and + "superior".

What is claimed is:

1. An agent for cleansing the skin which is a composition containing a liquid natural and/or synthetic water-based latex polymer emulsion, the polymer particle diameters being 0.05 to 5 μm, excluding styrene-butadiene latices, and at least one organic solvent, all the organic solvents in the composition having a lower volatility than ethanol and a boiling point >78.32° C. at 1.013 bar, and water.

2. The agent for cleansing the skin, according to claim 1, containing
   a) 10–80% by weight of the liquid natural and/or synthetic water-based latex emulsion,
   b) 1–15% by weight of the organic solvent having a lower volatility than ethanol and a boiling point >78.32° C.,
   c) 0–10% by weight of at least one surfactant,
   d) 0–10% by weight abrasives,
   e) 0–0.1% by weight thickener,
   f) optionally, cosmetic adjuvants and additives and/or active ingredients,
   g) 10–60% by weight water,
   the sum invariably being 100% by weight.

3. The agent for cleansing the skin according to claim 2, characterized in that the solvent is at least one polyhydric alcohol or derivative of a polyhydric alcohol, mono- or polyester of a saturated or unsaturated mono- or polyvalent carboxylic acid with 2 to 30 carbon atoms with n- and isoalkanols with 2 to 10 carbon atoms, and/or aliphatic hydrocarbon with 12 to 22 carbon atoms, preferably with 16 to 20 carbon atoms.

4. The agent for cleansing the skin according to claim 3, characterized in that the solvent is dipropylene glycol monomethyl ether.

5. The agent for cleansing the skin according to claim 3, characterized in that the latex emulsion is water-based polyisoprene.

6. The agent for cleansing the skin according to claim 5, characterized in that the solids content of the latex emulsion is 50 to 80% by weight.

7. The agent for cleansing the skin according to claim 6, characterized in that the latex emulsion has a cis-1,4 content of at least 90%.

8. The agent for cleansing the skin according to claim 7, characterized in that the particle size in the latex is 1.8 μm at maximum.

9. The agent for cleansing the skin according to claim 8 characterized in that the surfactant is a fatty alcohol ethoxylate of general formula R—O—$(CH_2$—$CH_2$—$O)_n$ with R=$C_{8-18}$ and n=1–8.

10. The agent for cleansing the skin according to claim 8, characterized in that the surfactant is a fatty alcohol ether sulfate of general formula: R—O—$(CH_2$—$CH_2$—$O)_n$ $SO_4X_2$ with R=$C_{10-16}$ and n-1–4 and X=$Na^{30}$, $K^+$, ½$Mg^{2+}$ or $NH_4^+$.

11. The agent for cleansing the skin according to claim 2 formulated as a hand washing paste.

12. A method of cleansing the skin, characterized in that the agent according to claim 1 is applied to the skin and distributed by rubbing in order to form particles which fall from the skin during further rubbing.

13. The method according to claim 12, characterized in that the cleansing takes place without the addition of water.

14. The agent for cleansing the skin, according to claim 1, containing
   a) 10–80% by weight of the liquid natural and/or synthetic water-based latex emulsion,
   b) 1–15% by weight of the organic solvent having a lower volatility than ethanol and a boiling point >78.32° C.,
   c) 0–10% by weight of at least one surfactant, which is a fatty alcohol ethoxylate, fatty alcohol ether sulfate, succinate, sarcoside and/or glucoside,
   d) 0–10% by weight an abrasive which is bleached walnut shell meal and/or non-swellable starch,
   e) 0–0.1% by weight thickener,
   f) optionally, cosmetic adjuvants and additives and/or active ingredients,
   g) 10–60% by weight water,
   the sum invariably being 100% by weight.

15. The agent for cleansing the skin according to claim 14, characterized in that the solvent is at least one solvent which is an alkylene glycol, a polyalkylene glycol, a polyalkylene glycol ether and/or polyalkylene glycol ester, a diester of aliphatic and/or aromatic di- and/or tricarboxylic acids, and/or aliphatic hydrocarbon with 12 to 22 carbon atoms.

16. The agent for cleansing the skin according to claim 15, characterized in that the solvent is dipropylene glycol monomethyl ether.

17. The agent for cleansing the skin according to claim 15, characterized in that the latex emulsion is water-based polyisoprene.

18. The agent for cleansing the skin according to claim 17, characterized in that the solids content of the latex emulsion is 60 to 70% by weight.

19. The agent for cleansing the skin according to claim 18, characterized in that the latex emulsion has a cis-1,4 content of at least 90%.

20. The agent for cleansing the skin according to claim 19, characterized in that the particle size in the latex is 1.8 μm at maximum.

21. The agent for cleansing the skin according to claim 20, characterized in that the surfactant is a fatty alcohol ethoxylate of general formula R—O—(CH$_2$—CH$_2$—O)n with R=C$_{8-18}$ and n=1–8.

22. The agent for cleansing the skin according to claim 20, characterized in that the surfactant is a fatty alcohol ether sulfate of general formula: R—O—(CH$_2$—CH$_2$—O)$_n$SO$_4$X$_2$ with R=C$_{10-16}$ and n=1–4 and X=Na$^+$, K$^+$, ½Mg$^{2+}$ or NH$_4^{30}$.

23. The agent for cleansing the skin according to claim 21 or 22, characterized in that the solvent is dipropylene glycol monomethyl ether.

* * * * *